United States Patent [19]

Young

[11] Patent Number: 4,664,717

[45] Date of Patent: * May 12, 1987

[54] METHODS FOR HYDROLYZING POLYSACCHARIDES AND COMPOSITIONS USEFUL THEREIN

[75] Inventor: Donald C. Young, Fullerton, Calif.

[73] Assignee: Union Oil Company of California, Los Angeles, Calif.

[*] Notice: The portion of the term of this patent subsequent to Apr. 23, 2002 has been disclaimed.

[21] Appl. No.: 673,358

[22] Filed: Nov. 20, 1984

Related U.S. Application Data

[63] Continuation-in-part of Ser. No. 455,268, Jan. 3, 1983, abandoned, and a continuation-in-part of Ser. No. 455,317, Jan. 3, 1983, and a continuation-in-part of Ser. No. 442,296, Nov. 17, 1982, and a continuation-in-part of Ser. No. 444,667, Nov. 26, 1982, and a continuation-in-part of Ser. No. 453,282, Dec. 27, 1982, Pat. No. 4,522,644, and a continuation-in-part of Ser. No. 453,496, Dec. 27, 1982.

[51] Int. Cl.$^4$ ............................ C13K 1/06; C13K 1/02
[52] U.S. Cl. ........................................ 127/37; 127/38; 127/42
[58] Field of Search ...................... 127/36, 37, 38, 39, 127/42

[56] References Cited

U.S. PATENT DOCUMENTS

| Re. 1,995 | 6/1865 | Hoffmann | 127/36 |
|---|---|---|---|
| 1,878,852 | 9/1932 | Hoppler | 127/36 |
| 1,917,539 | 7/1933 | Miles | 127/37 |
| 1,919,623 | 7/1933 | Dreyfus | 127/37 |
| 2,767,108 | 10/1956 | Fetzer | 127/36 X |
| 4,116,664 | 9/1978 | Jones | 71/549 |
| 4,214,888 | 7/1980 | Young | 71/28 |
| 4,315,763 | 2/1982 | Stoller et al. | 71/29 |
| 4,397,675 | 8/1983 | Young | 71/28 |
| 4,402,852 | 9/1983 | Young | 252/182 |
| 4,404,116 | 9/1983 | Young | 252/182 |
| 4,447,253 | 5/1984 | Young | 71/28 |
| 4,512,813 | 4/1985 | Young | 134/27 |
| 4,589,925 | 5/1986 | Young | 134/3 |

OTHER PUBLICATIONS

Science News, vol. 123, No. 23, Jun. 4, 1983, p. 366, Science Service, Inc., 1719 N. St. N.W., Washington, D.C. "Cellulose Digestion" by Lab Bacteria.
The Condensed Chemical Dictionary, Seventh Edition, Van Nostrand Reinhold Company, New York, 1969, p. 908.
D. F. duToit, Verslag Akad. Wetenschappen, 22, 5/3–4 (abstrated in Chemical Abstracts, 8, 2346, (1914).
L. H. Dalman, "Ternary Systems of Urea and Acids. I. Urea, Nitric Acid and Water. II. Urea, Sulfuric Acid and Water. III. Urea, Oxalic Acid and Water; JACS 56, 549–53 (1934).
Sulfur Institute Bulletin No. 10 (1964), "Adding Plant Nutrient Sulfur to Fertilizer".

Primary Examiner—Richard V. Fisher
Assistant Examiner—W. Gary Jones
Attorney, Agent, or Firm—Michael H. Laird; Greg Wirzbicki; Dean Sandford

[57] ABSTRACT

Polysaccharides are at least partially hydrolyzed by contact with a composition containing urea, sulfuric acid, and water in which the urea/sulfuric acid molar ratio is less than 2. Such proportions of urea and sulfuric acid assure the presence of the monourea adduct of sulfuric acid. The polysaccharide can be hydrolyzed to an extent sufficient only to hydrate the polysaccharide to produce a hydrated polysaccharide such as hydrated cellulose, or it can be completely hydrolyzed to its constituent monosaccharides. Thus, cellulose can be converted to glucose.

35 Claims, No Drawings

METHODS FOR HYDROLYZING POLYSACCHARIDES AND COMPOSITIONS USEFUL THEREIN

RELATED APPLICATIONS

This application is a continuation-in-part of my co-pending applications Ser. No. 455,268, Cellulosic Composition and Method for Treating Cellulosic Materials, filed Jan. 3, 1983, now abandoned; Ser. No. 455,317, Plant Seed Compositions and Methods for Treating Plant Seeds, filed Jan. 3, 1983; Ser. No. 442,296, Systemic Herbicidal Compositions and Methods of Use, filed Nov. 17, 1982; Ser. No. 444,667, Methods for Controlling Vegetation, filed Nov. 26, 1982; Ser. No. 453,282, Methods for Selectively Controlling Plant Suckers, filed Dec. 27, 1982 now U.S. Pat. No. 4,522,644; and Ser. No. 453,496, Acid-Catalyzed Reactions and Compositions for Use Therein, filed Dec. 27, 1982.

BACKGROUND

1. Field of the Invention

This invention relates to the field of polysaccharide hydrolysis and, in particular, it relates to methods and compositions useful for the partial hydrolysis (including hydration) of polysaccharides and to the complete hydrolysis of polysaccharides to form monosaccharides.

2. Description of the Art

The uses for partially and completely hydrolyzed polysaccharides are many and various. Sugars (primarily mono- and disaccharides) are used as foods and in foods for sweetening and food value, for the manufacture of syrups, confectioneries, preserves, etc.; as demulcents and lenitives; in the manufacture of soaps, pharmaceutical products, chemical intermediates for detergents, emulsifying agents, plasticizers, resins, explosives, glues, insecticides, and other products. One use for sugars, which is of current importance, is in their conversion by chemical or enzymatic processes to alcohols which are useful as fuels and fuel additives and in the manufacture of plastics, synthetic rubber, pharmaceuticals, and other chemical products. Partially hydrolyzed polysaccharides, including hydrated polysaccharides such as hydrated cellulose, are also useful in a variety of applications including the manufacture of glycogen, processed starch, and as chemical precursers for the manufacture of paper, fibers (including vulcanized fibers, mercerized cotton, and viscose rayon), and others.

While millions of pounds of various sugars (principally mono- and disaccharides such as glucose, sucrose, fructose, and maltose) are produced annually, most lower molecular weight mono- and polysaccharides, such as the sugars, are chemically bound into high molecular weight polysaccharides such as carbohydrates and animal and plant starches. By far the most abundant polysaccharide is cellulose which is the basic building block of all vegetable matter, and which is grown, harvested, and disposed of in immense quantities. Approximately 900 million metric tons of cellulose wasate (including discarded paper, crop stubbles such as corn stalks, rice stubble, etc., and sawdust) are produced in the United States each year. An immerse quantity of potential energy in the form of glucose is locked into this cellulose waste, and the great advantage to be gained by releasing that energy in the form of glucose has not gone unnoticed.

Several methods have been suggested for hydrolyzing higher molecular weight polysaccharides, such as cellulose, to their partially or completely hydrolyzed subunits such as glucose, and several are practiced commercially. For instance, it is known that polysaccharides, such as cellulose, can be hydrolyzed by the action of a strong base such as sodium hydroxide and calcium hydroxide. However, reaction rates are very slow, particularly at lower temperatures. Thus, economic production of base-hydrolyzed polysaccharides requires long contact times, high caustic concentrations (and cost) and relatively high temperatures on the other of 300° F. (which requires the use of pressurized treating vessels). Furthermore, base is consumed in such processes in amounts proportionate to the amount of product obtained. A variety of bacterial and enzymatic processes also is known. For instance, it is known that papyan enzyme, if present in sufficient quantities, will gradually hydrolyze cellulose to glucose. It is also known that certain bacteria, such as Thermomonospora, which contain cellulase enzyme can convert cellulose to glucose for use by the bacteria, and that the cellulase enzyme, if isolated, might be employed to obtain glucose from cellulose. It is also known that the severe hydrolysis of polysaccharides, such as cellulose, with strong mineral acids, such as sulfuric acid, can be controlled to yield some glucose. However, dehydration and oxidation side reactions decrease the yield of glucose or other saccharide from the polysaccharide feed and consume the hydrolyzing agent, e.g., sulfuric acid, as illustrated in the following expression:

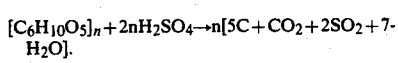

$$[C_6H_{10}O_5]_n + 2nH_2SO_4 \rightarrow n[5C + CO_2 + 2SO_2 + 7H_2O].$$

Accordingly, a significant need exists for improved processes for partially or completely hydrolyzing polysaccharides to form hydrated polysaccharides, lower molecular weight polysaccharides, and/or monosaccharides.

It is therefore one object of this invention to provide improved methods and compositions for hydrolyzing polysaccharides.

Another object is the provision of methods and compositions for producing lower molecular weight polysaccharides from higher molecular weight polysaccharides.

Another object of this invention is the provision of methods and compositions useful for converting polysaccharides to monosaccharides.

Yet another object is the provision of methods and compositions useful for converting cellulose to hydrated cellulose.

Another object is the provision of methods and compositions useful for converting cellulose to glucose.

Other objects, aspects, and advantages of this invention will be apparent to one skilled in the art in view of the following disclosure and the appended claims.

SUMMARY OF THE INVENTION

Briefly, the invention provides novel methods for partially or completely hydrolyzing polysaccharides and compositions useful in such methods. More specifically, the novel methods involve contacting a polysaccharide containing 2 or more saccharide subunits with urea, sulfuric acid, and water in proportions such that the urea/sulfuric acid molar ratio is less than 2. The polysaccharide can be partially hydrolyzed to form a hydrated polysaccharide such as hydrated cellulose, a lower molecular weight polysaccharide, or the corresponding monosaccharide. The novel compositions involve combinations of one or more polysaccharides, urea, sulfuric acid, and water, in proportions which correspond to a urea/sulfuric acid molar ratio less than 2. These compositions optionally also can contain surfactants and/or non-aqueous polar solvents (in addition to other components).

DETAILED DESCRIPTION OF THE INVENTION

The polysaccharides which can be treated in accordance with the methods of this invention, and which can comprise components of the novel compositions, include all natural and synthetic, virgin, manufactured, and/or chemically pretreated polysaccharides which contain more than 1 saccharide unit per molecular. Thus, the methods of this invention can be employed to hydrolyze all carbohydrates which contain more than one saccharide unit per molecular including oligosaccharides, which are conventionly characterized as polysaccharides having 2 to 8 saccharide units per molecular, and higher molecular weight polysaccharides such as cellulose, rayon, vegetable starches, animal starches (glycogen), etc.

Polysaccharides and monosaccharides make up the group of compounds known as carbohydrates which are polyhydroxy aldehydes, polyhydroxy ketones, or compounds that can be hydrolyzed to form such compounds. By definition, monosaccharides are carbohydrates which cannot be hydrolyzed to simpler compounds. As used in this disclosure, the term polysaccharides connotes carbohydrates which can be hydrolyzed to 2 or more monosaccharide molecules.

Monosaccharides can contain either aldehyde or keto groups; the former being known as aldoses, the latter as ketoses. glucose, produced as such and "locked" in its hydrolyzable polymeric form—cellulose—is the most abundant aldose. Fructose (fruit sugar) is one of the more common ketoses which is combined with glucose in the disaccharide, sucrose (common table sugar). Other common disaccharides include maltose (malt sugar), cellobiose, and lactose (milk sugar). Maltose is the major constituent of starch and can be obtained from starch by partial hydrolysis. Cellobiose, similarly, can be derived from cellulose such as cotton fibers by partial hydrolysis and can be further hydrolyzed to glucose. Lactose, the disaccharide of glucose and galactose, constitutes approximately 5 weight percent of cow's milk and is obtained commercially from whey, a by-product of cheese manufacture. Sucrose, common table sugar, is generally obtained from sugar cane and sugar beets and can be hydrolyzed to its constituent monosaccharides—glucose and fructose.

Most polysaccharides are naturally occurring polymers containing one or more different monosaccharide subunits (although synthetic forms are known) and can be made up of hundreds or even thousands of monosaccharide units per molecular. The monosaccharide units in di- and higher polysaccharides are joined through glycoside linkages which can be broken by hydrolysis. Cellulose and plant and animal starches are by far the most abundant polysaccharides.

Illustrative of sources of polysaccharides which can be employed in the methods and compositions of this invention are wood; paper; plant matter including crop foliage and stubble such as mown grass, hay, rice and corn stubble, wood scrap, sawdust, cottom (either virgin or from scrap clothing or other textile products), vegetable scrap; and plant and animal starches.

The polysaccharide sources employed in the methods and compositions of this invention can be either untreated or chemically pretreated by one or more unrelated chemical or manufacturing processes or by processes which facilitate hydration such as chemical treatment to remove hydrophobic substances such as lignins or to partially hydrate the polysaccharide source. Such polysaccharide sources, if not soluble in the urea-sulfuric acid-hydrolyzing component employed in this invention, are preferably finely divided prior to treatment or incorporation into the compositions of this invention. Thus, finely divided materials such as sawdust, cotton fiber, shredded paper, shredded vegetable matter, etc., are ideal polysaccharide sources. Other sources such as larger wood particles and corn stubble are preferably ground or shredded prior to treatment to increase their surface area. High surface area is particularly preferred for polysaccharide sources which contain hydrophobic components such as lignins in order to facilitate contact of the useful urea-sulfuric acid hydrolyzing agents with the polysaccharide.

Lignins may optionally be removed from lignin-containing polysaccharide sources prior to hydrolysis by known chemical treatments. Lignins can be removed from cellulosic materials by extraction with liquid ammonia or sodium or ammonium bisulfite, procedures which are practiced in the paper pulp manufacturing industry. Liquid or pressurized ammonia treatment ammoniates and liquid ammonia extracts lignins from cellulose, while sulfite treatment converts lignins to forms which are water extractable. Lignins can also be removed by the so-called Kraft process which involves lignin sulfonation by reaction with sulfur dioxide followed by water extraction.

The useful urea-sulfuric acid hydrolyzing agents are combinations of urea, sulfuric acid, and water (in the presence or absence of other components) in which the urea/sulfuric acid molar ratio is less than 2. Such proportions of urea and sulfuric acid assure that at least a portion of the sulfuric acid is present as the monourea adduct of sulfuric acid. I have found that the monourea adduct of sulfuric acid efficiently and rapidly hydrolyzes polysaccharides in the presence of water. The monourea adduct is not present when the urea/sulfuric acid molar ratio is 2 or more. In such compositions all of the sulfuric acid is present as the diurea adduct. The diurea adduct of sulfuric acid has little or no polysaccharides-hydrolyzing activity. I have also found that the monourea-sulfuric acid adduct does not promote undesirable side reactions which are characteristic of sulfuric acid-polysaccharide reactions such as sulfonation, oxidation, and dehydration. Such side reactions unavoidably cause the loss of polysaccharide feed and sulfuric acid reagent.

Accordingly, the useful hydrolyzing components will usually have urea/sulfuric acid molar ratios of at least about ¼ and less than 2, generally about ¼ to about 7/4. The more preferred compositions which contain less uncomplexed sulfuric acid have urea/sulfuric acid molar ratios of at least about ½, generally about ½ to about 3/2. The most preferred hydrolyzing agents have urea/sulfuric acid molar ratios of at least about 1/1 such that all of the sulfuric acid is complexed with urea as either the mono- or diurea adduct. It is also preferable to assure that a substantial portion of the sulfuric acid is present as the mono- rather than the diurea adduct. Thus, the most preferred compositions are those which have urea/sulfuric acid molar ratios within the range of about 1/1 to about 3/2.

The concentration of urea and sulfuric acid in the water-containing hydrolyzing agent should be sufficient to promote the polysaccharide hydrolysis, and I have found that catalytic amounts of urea and sulfuric acid, i.e., less than about 1 weight percent in aqueous solution, are sufficient for this purpose. However, higher urea-sulfuric acid concentrations produce hgiher rates of hydrolysis and are often preferred. Accordingly, the urea and sulfuric acid, in combination, will usually constitute at least about 1, generally at least about 5, and preferably about 5 to about 99.8 weight percent of the combination of urea, sulfuric acid, and water. The most preferred compositions are those in which the urea and sulfuric acid, in combination, constitute at least about 10 weight percent, usually 10 to about 99.8 weight percent of the combination of urea, sulfuric acid, and water.

Water reacts with the polysaccharide in the course of the hydrolysis reaction in amounts which appear to correspond to 1 mole of water per mole of monosaccharide produced (when hydrolysis is carried completely to the production of monosacharides) and, accordingly, is present in the useful hydrolyzing agents in at least minor concentrations of at least about 0.2 weight percent. However, the useful hydrolyzing agents can also be very dilute, i.e., they can have a high water concentrations of up to 99 weight percent water or more. Accordingly, water concentration will usually be within the range of 0.2 to about 99 weight percent, generally about 0.2 to about 90 weight percent, and preferably about 5 to about 90 weight percent based on the combined weight of urea, sulfuric acid, and water.

As discussed in by copending Ser. No. 673,508, Thermally Stable Urea Sulfuric Acid Compositions and Methods of Manufacture, filed Nov. 20, 1984, the disclosure of which is incorporated herein by reference, urea-sulfuric acid compositions which have less than about 1 weight percent water are much more stable thermally than are compositions which contain substantially higher water concentrations. For instance, urea-sulfuric acid compositions having urea/sulfuric acid molar ratios of about 1 which contain about 10 weight percent water have incipient decomposition temperatures of about 176° F. (80° C.) and decompose explosively at about 190° to 200° F. (about 90° C.). Incipient decomposition temperature is that temperature at which the urea-sulfuric acid component begins to decompose as indicated by effervescence ($CO_2$ evolution) and/or discoloration of the composition, as discussed in my above referenced copending applications. In contrast, otherwise identical urea-sulfuric acid compositions which contain about 1 weight percent water or less can be heated to temperatures above 80° C. and even above 90° or 100° C. without incipient decomposition. The advantages of employing such low water-content compositions are evident when it is desired to conduct the hydrolysis reaction of this invention at temperatures of 80° C. or higher.

The useful urea-sulfuric acid-water hydrolyzing agents may optionally contain other components which do not negate the activity of the hydrolyzing agents for the hydrolysis of polysaccharides. In fact, the use of hydrolyzing agents which contain polar solvents (other than water) and/or surfactants is sometimes preferred, particularly for the treatment for polysaccharide feeds which contain hydrophobic substances such as lignins and/or fatty materials such as lipids. Illustrative solvents include organic and inorganic solvents in which both urea and sulfuric acid are soluble such a dimethyl sulfoxide; alcohols, e.g., methanol, glycol, acetone, methylethyl ketone, tetrahydrofuran; halogenated hydrocarbons such as trichloromethane and chloroform, and the like.

One or more of such polar solvents can be present over a wide range of concentrations, usually within the range of about 2 to about 95 weight percent based on the combiend weight of solvent, urea, sulfuric acid, and water. Illustrative suitable surfactants are discussed in my copending application Ser. No. 453,496 referred to above, which is incorporated herein by reference in its entirety. Surfactants can also be employed over a wide range of concentrations. Useful concentrations are usually at least about 0.1 and generally about 0.1 to about 10 weight percent surfactant based on the combined weight of surfactant, urea, sulfuric acid, water, and polar solvent (if present).

The useful urea-sulfuric acid-containing hydrolyzing agents can be prepared by any one of the variety of procedures. One suitable procedure for preparing urea-sulfuric acid components which are free of thermal decomposition products is disclosed in my application Ser. No. 318,629, Methods of Producing Concentrated Urea-Sulfuric Acid Reaction Products, filed Nov. 5, 1981, now U.S. Pat. No. 4,445,925, which is incorporated herein by reference in its entirety. The urea-sulfuric acid component can also be obtained by gradually adding urea to sulfuric acid or vice versa, in the presence or absence of water and/or other solvent. Sufficient cooling must be provided to assure that the urea-sulfuric acid component does not thermally decompose. In another alternative, the urea or sulfuric acid can be added to a dispersion or solution of the other component and the polysaccharide feed material in water or other solvent, again, with the provision that sufficient cooling is provided to prevent thermal decomposition. In this alternative, it is presently preferred that the urea be added to the polysaccharide dispersion or solution before sulfuric acid is added so that the urea is present to react with the sulfuric acid upon its addition, thereby minimizing reaction of free sulfuric acid with the polysaccharide. However, it is presently most preferred that the urea-sulfuric acid component be preformed prior to mixing with the polysaccharide in order to prevent the reaction of free sulfuric acid with the polysaccharide feed.

The relative proportions of urea, sulfuric acid, water, and polysaccharide can vary considerably depending upon the reaction rate and extent of hydrolysis desired. As mentioned previously, the urea and sulfuric acid act primarily as catalysts and are not consumed in the hydrolysis reaction (although they may be consumed by reaction with impurities). Thus, it is necessary only that the urea and sulfuric acid be present in catalytic amounts. However, I have found that reaction rate increases as the urea and sulfuric acid concentrations are increased. Thus higher reaction rates can be achieved at higher urea-sulfuric acid concentrations. Accordingly, the urea and sulfuric acid, in combination, will usually be present in amounts of at least about 0.5, generally at least about 1, and preferably at least about 5 weight percent based on the combined weight of urea, sulfuric acid, water, and polysaccharide. The majority of reaction conditions will involve urea-sulfuric acid concentrations within the range of about 1 to about 90 weight percent, preferably about 5 to about 50 weight percent based on urea, sulfuric acid, water, and polysaccharide.

Water is a reactant and is consumed in the hydrolysis reaction in proportion to the number of moles of water added to the polysaccharide feed. For instance, the hydrolysis of one monosaccharide unit in a polysaccharide molecule to form one free monosaccharide molecule requires the consumption of one molecule of water. Accordingly, the water concentration employed in the hydrolysis reaction should be sufficient to supply the amount of water required to effect the desired degree of hydrolysis. All of the water either can be added initially, or it can be added incrementally during the reaction to replace water consumed by hydrolysis. Accordingly, the concentration of water present in the hydrolysis reaction at any given time is generally at least about 0.1 weight percent and can range up to as high as 95 weight percent or more based on the combined weight of urea, sulfuric acid, water, and polysaccharide. Within this range, the water concentration is generally determined by the desired proportion of water relative to urea and sulfuric acid which is discussed above.

Water concentration can be employed to control the rate and extent of hydrolysis since its presence is necessary for the progress of the hydrolysis reaction. Accordingly, initial water concentrations of one weight percent or less based on polysaccharide can be employed to assure that no more than one weight part of water per 100 weight parts of polysaccharide will be added to the polysaccharide by hydrolysis. Higher or lower initial water concentrations can be employed to effect varying degrees of hydrolysis. Furthermore, the water concentration in the hydrolysis reaction can be maintained at a relatively low level and incrementally or continuously supplemented to maintain that level as water is consumed in order to control the rate of hydrolysis as desired.

The polysaccharide can be contacted with the urea-sulfuric acid hydrolysis agent, and water, in the presence or absence of other components, by any procedure capable of accomplishing the desired degree of contact of these respective components. For instance, the urea-sulfuric acid component can be added to a solution or dispersion of the polysaccharide in water, or a water-containing urea-sulfuric acid component can be sprayed onto finely divided polysaccharide-containing feed material. In the alternative, the polysaccharide feed can be immersed in a water-containing solution or melt of the urea-sulfuric acid component. Light misting of a polysaccharide-containing feed with a water-containing urea-sulfuric acid component can be employed to effect minor amounts of hydration on the surface of the polysaccharide feed.

The hydrolysis reaction can be conducted over a wide range of temperatures which are sufficient to maintain the urea-sulfuric acid-water component in the form of a solution or melt and which do not exceed the thermal decomposition of the urea-sulfuric acid component. The more concentrated urea-sulfuric acid-water mixtures, i.e., those in which the urea and sulfuric acid, in combination, constitute 30 percent or more of the combination, will crystalize and/or will become solids at temperatures much below 0° C. The maximum temperature is preferably maintained at a point below the incipient decomposition temperature of the urea-sulfuric acid component as discussed previously. Accordingly, hydrolysis temperatures will usually be at least about 0° C., generally at least about 10° C., and preferably within the range of about 20° to about 80° C., particularly when employing compositions which contain substantially more than one weight percent water. As discussed above, urea-sulfuric acid components which contain about one weight percent water or less have incipient decomposition temperatures above 80° C. Accordingly, such compositions can be employed in the hydrolysis reaction at temperatures above 80° C., or even above 100° C. or higher.

Higher reaction temperatures increase the rate of hydrolysis; thus, reaction temperature can be employed to control hydrolysis rate. For instance, the rate of hydrolysis of most polysaccharides in the presence of the urea-sulfuric acid-water components is relatively low at temperatures of about 10° C. and below; thus, such temperatures can be employed ot hydrolyzed the polysaccharide feed at a relatively slow rate when that result is desired.

The reaction should be continued for a period of time sufficient to hydrolyze at least a portion of the polysaccharide feed, and longer reaction times can be employed when complete hydrolysis is desired. Thus, when only nominal degrees of hydration are desired (such as in the production of hydrated cellulose), short reaction times, relatively low reaction temperatures, low urea-sulfuric acid concentrations, low water concentrations, and/or low surfactant concentrations can be employed to achieve that result. Most often, however, it is preferable to effect hydration of at least about 50 percent of the polysaccharide to its constituent monosaccharides, and, when the production of monosaccharides is the essential object of the reaction, it is preferable to continue the hydrolysis reaction until essentially all, i.e., 100 percent of the polysaccharide, has been converted to monosaccharides. Accordingly, the hydrolysis reaction will usually be allowed to continue for at least about 1 minute, generally at least about 5 minutes, with most reactions involving reaction times of about 5 minutes to about 100 hours. Reaction times of about 10 minutes to about 2 hours under otherwise moderate conditions, e.g., moderate temperatures of 20° to 60° C., are sufficient to effect complete hydrolysis of many polysaccharide sources such as cotton and other plant matter such as rice stubble, corn stubble, and the like. For instance, 400 grams of cotton can be completely converted to glucose in one hour at 25° C. by immersion in 500 grams of a 1/1/1 molar ratio mixture of urea, sulfuric acid, and water, respectively, diluted with an additional 45 grams of water.

The hydrolysis reaction can be terminated, if desired, by diluting the reactant-polysaccharide mixture, separating the polysaccharide from the remaining reactants, and/or neutralizing the sulfuric acid reactant. The reactant-polysaccharide mixture can be diluted with water and/or other solvents or diluents to the point that the concentration of the urea-sulfuric acid component becomes very low with a consequent reduction in reaction rate. Separation of the polysaccharide from the remaining reactants can be effected by washing, or extracting the polysaccharide from the reactants, or by crystalizing the urea-sulfuric acid component at low temperatures. Neutralization of the sulfuric acid can be effected by the addition of any suitable organic or inorganic base such as ammonia, sodium hydroxide, calcium hydroxide, amines, and the like.

Following the completion of the reaction, the reactant mixture containing partially and/or completely hydrolyzed polysaccharide can be employed as animal feed, or as a fermentation medium for the production of fermentation products such as alcohols, or it can be separated to isolate monosaccharide and/or partially hydrolyzed polysaccharide product.

The reaction mixture containing partially or completely hydrolyzed polysaccharides also contains urea and sulfuric acid and can be employed directly as feed for animals, such as ruminant mammals, which can tolerate the urea concentrations remaining in the composition (provided, of course, that the composition does not contain imcompatible solvents or diluents). Optionally, the reactant composition can be neutralized prior to feeding by the addition of stoichiometric or excess quantities of ammonia, sodium hydroxide, or non-toxic other organic or inorganic bases.

Reaction products which contain monosaccharides and/or partially hydrated polysaccharides also can be employed directly as fermentation media for the manufacture of alcohols and other fermentation products by known enzymatic and/or bacterial processes. The fermentation product can be neutralized prior to exposure to acid-sensitive bacteria or other components of the fermentation media by the addition of appropriate organic or inorganic bases such as ammonia, sodium hydroxide, magnesium hydroxide, etc., some of which serve as nutrients for fermentation bacteria. The resulting alcohol product can be separated by distillation, and the residue can be employed as a high nitrogen fertilizer or animal feed supplement.

Partially hydrolyzed polysaccharides (such as hydrated cellulose and partially hydrolyzed sawdust, wood fibers, paper, and/or vegetable matter) which have not been sufficiently hydrated to become dissolved in the reaction medium can be separated from the urea-sulfuric acid component and other components of the reaction medium by conventional physical separation means such as filtration, centrifuging, decanting, and, optionally, can be further purified by washing with water or other solvent.

Monosaccharides and/or lower molecular weight polysaccharides soluble in the reaction medium (e.g., polysaccharides containing 2 to about 100 saccharide units per molecule) can be recovered from the reaction medium by procedures such as crystallization and/or solvent extraction. Such materials can be crystallized from relatively concentrated solutions, e.g., solutions containing 10 weight percent solute or more, by reducing solution temperature to less than 20° C. or less than 0° C. or below. Crystallized material can be recovered by physical separation means such as filtration, centrifuging, and the like, and the supernatant phase containing urea, sulfuric acid, water, and optionally other solvents or diluents, can be recycled to the hydration reaction.

In the alternative, product monosaccharides and lower molecular weight polysaccharides can be recovered by extraction with appropriate solvents including ethers such as tetrahydrofuran, diethyl ether, methylethyl ether, etc., and/or chlorinated hydrocarbons such as methyl chloride, trichloroethane, perchloroethane, carbon tetrachloride, etc. Recovery of the monosaccharide and/or lower molecular weight polysaccharide from the extraction solvent can be effected by conventional means such as low temperature crystallization or by solvent distillation.

The invention is further described by the following examples which are illustrative of specific modes of practicing the invention and are not intended as limiting the scope of the invention as defined by the appended claims.

EXAMPLE 1

400 grams of cotton fiber were immersed in 545 grams of a solution containing 31.3 weight percent urea, 51.1 weight percent sulfuric acid, and 17.6 weight percent water, and the mixture was stirred at room temperature (about 23° C.) for one hour. The urea and sulfuric acid, in combination, constituted 82.4 weight percent of the solution and 47.5 weight percent of the mixture of polysaccharide (cotton), urea, sulfuric acid, and water, and the relative proportions of urea and sulfuric acid corresponded to a urea/sulfuric acid molar ratio of 1. During the one hour reaction period, the cotton "dissolved" to produce a colorless syrup. There was no evidence of significant heat or of any gas evolution, and titration of the product mixture with standard base indicated that the final acid concentration was the same as the initial acid concentration. Thus, no acid consumption had occurred. Analyses of the product established that it was composed of glucose and the starting urea-sulfuric acid adduct.

EXAMPLE 2

Sawdust from which the lignins have been removed by liquid ammonia treatment can be partially hydrolyzed by immersing 100 grams of the treated sawdust in 500 grams of the urea-sulfuric acid-water solution described in Example 1 for 2 minutes at 50° C. The partially hydrolyzed sawdust then can be separated by filtration and further purified by water washing.

EXAMPLE 3

Rice stubble can be converted to glucose by immersing 50 grams of finely ground rice stubble in 200 grams of an aqueous solution containing 20 weight percent urea, 32 weight percent sulfuric acid, and 48 weight percent water and agitating the resulting mixture at 40° C. for one hour.

Numerous variations and modifications of the concepts of this invention will be apparent to one skilled in the art in view of the aforegoing disclosure and the appended claims and are intended to be encompassed within the scope of this invention defined by the following claims.

I claim:

1. A method for at least partially hydrolyzing a polysaccharide which comprises contacting said polysaccharide, in the presence of water, with a composition comprising urea and sulfuric acid, in which composition the urea/sulfuric molar ratio is at least about ¼ and less than 2.

2. The method defined in claim 1 wherein said urea/sulfuric acid molar ratio is about ½ to 3/2.

3. The method defined in claim 1 wherein said urea/sulfuric acid molar ratio is at least about 1/1.

4. The method defined in claim 1 wherein said urea and sulfuric acid, in combination, constitute at least about 1 weight percent of said composition, and said urea/sulfuric acid molar ratio is at least about ½.

5. The method defined in claim 1 wherein said urea and sulfuric acid, in combination, constitute about 5 to about 99.8 weight percent of said composition.

6. The method defined in claim 1 wherein said composition further comprises a surfactant.

7. The method defined in claim 1 wherein said composition further comprises a non-aqueous solvent.

8. The method defined in claim 1 wherein said polysaccharide comprises cellulose.

9. The method defined in claim 8 wherein said cellulose comprises a member selected from the group consisting of treated and untreated wood, paper, plant matter, and combination thereof.

10. The method defined in claim 1 wherein said polysaccharide comprises a member selected from the group consisting of glycogen and plant starches, and combinations thereof.

11. The method defined in claim 1 wherein said polysaccharide is contacted with said composition at a temperature below the incipient decomposition temperature of said composition.

12. The method defined in claim 1 wherein said polysaccharide comprises cellulose and is contacted with said composition under conditions sufficient to partially hydrate said cellulose.

13. The method defined in claim 12 which further comprises a step of recovering the resulting partially hydrated cellulose from said composition.

14. The method defined in claim 1 wherein said polysaccharide comprises cellulose and is contacted with said composition under conditions sufficient to hydrolyze at least a portion of said cellulose to glucose.

15. The method defined in claim 14 wherein said polysaccharide is contacted with said composition at at temperature of at least about 20° C. for a period of at least about 5 minutes sufficient to hydrolyze at least 50 percent of said cellulose to glucose.

16. The method defined in claim 15 which further comprises the step of recovering said glucose from said composition.

17. The method defined in claim 15 wherein polysaccharide is contacted with said composition under conditions sufficient to convert about 50 to 100 percent of said cellulose to glucose, and which method further comprises the step of recovering the resulting glucose from said composition.

18. The method defined in claim 1 wherein said polysaccharide is contacted with said composition under conditions sufficient to hydrolyze at least a portion of said polysaccharide to its constituent monosaccharide.

19. The method defined in claim 18 wherein said polysaccharide is contacted with said composition at a temperature of at least about 20° C. for a period of at least about 5 minutes sufficient to hydrolyze at least 50 percent of said polysaccharide to its constituent monosaccharide.

20. The method defined in claim 18 wherein said polysaccharide is contacted with said composition under conditions sufficient to convert about 50 to 100 percent of said polysaccharide to its constituent monosaccharide.

21. The method defined in claim 20 wherein said polysaccharide is selected from the group consisting of animal starch, plant starch, and combinations thereof.

22. The method defined in claim 1 wherein said composition comprises less than about 1 weight percent water, and said polysaccharide is contacted with said composition at a temperature of at least 80° C.

23. The method defined in claim 1 wherein said composition comprises less than about 1 weight percent water, and said polysaccharide is contacted with said composition at a temperature of at least about 90° C.

24. The method defined in claim 1 wherein said polysaccharide is contacted with said composition in a proportion corresponding to at least about 0.5 weight percent urea and sulfuric acid, taken in combination, based on the combined weight of said urea, sulfuric acid, and polysaccharide.

25. The method defined in claim 1 wherein said polysaccharide is contacted with said composition in proportions corresponding to at least about 5 weight percent of said urea and sulfuric acid, taken in combination, based on the combined weight of said urea, sulfuric acid, and polysaccharide.

26. A method of hydrolyzing cellulose to glucose which method comprises the step of contacting a composition comprising cellulose, in the presence of water, with a hydrolyzing agent comprising urea and sulfuric acid in which the urea/sulfuric acid molar ratio is at least $\frac{1}{4}$ and less than 2.

27. The method defined in claim 26 which further comprises the step of recovering the resulting glucose from said composition.

28. The method defined in claim 26 wherein said urea/sulfuric acid molar ratio is at least about $\frac{1}{2}$, said urea and said sulfuric acid, in combination, constitute at least about 5 weight percent of said hydrolyzing agent, and said cellulose is contacted with said hydrolyzing agent in proportions corresponding to at least 1 weight percent of said urea and sulfuric acid, taken in combination, based on the combined weight of said cellulose, urea, and sulfuric acid.

29. The method defined in claim 26 wherein said urea/sulfuric acid molar ratio is at least about 1, and said urea and said sulfuric acid, in combination, constitute about 10 to about 99.8 weight percent of said hydrolyzing agent and at least about 5 weight percent of the resulting combination of said cellulose and said hydrolyzing agent.

30. The method defined in claim 26 wherein said water comprises less than about 1 weight percent of said hydrolyzing agent, and said composition is contacted with said cellulose at a temperature of at least 80° C.

31. A method for hydrolyzing cellulose to glucose, which method comprises the step of contacting a composition which comprises cellulose with a hydrolyzing agent comprising urea, sulfuric acid, and water in which the urea/sulfuric acid molar ratio is within the range of about $\frac{1}{2}$ to less than 2, said urea and said sulfuric acid, in combination, constitute at least about 10 weight percent of said hydrolyzing agent, said water comprises at least about 5 weight percent of said hydrolyzing agent, and said hydrolyzing agent and said cellulose are contacted in proportions corresponding to at least about 1 weight percent of said urea and sulfuric acid, taken in combination, and at least about 1 weight percent of said cellulose, for a period of at least about 5 minutes sufficient to hydrolyze at least a portion of said cellulose to glucose.

32. A method for hydrolyzing a polysaccharide which method comprises contacting said polysaccharide, in the presence of water, with a composition comprising urea and sulfuric acid in which the urea/$H_2SO_4$ molar ratio is about $\frac{1}{2}$ to less than 2 under conditions sufficient to at least partially hydrolyze said polysaccharide, and recovering the at least partially hydrolized polysaccharide.

33. The method defined in claim 32 wherein the molar ratio of said urea to said sulfuric acid in said composition is at least about 1.

34. A method for hydrolyzing cellulose to glucose which method comprises the step of contacting a composition comprising cellulose, urea, sulfuric acid, and water, and having a urea/$H_2SO_4$ molar ratio of about ½ to less than 2 under conditions sufficient to hydrolyze at least a portion of said cellulose to glucose.

35. A method for producing hydrated cellulose, which method comprises the steps of contacting a composition comprising cellulose, urea, sulfuric acid, and water, in which composition the molar ratio of said urea to said sulfuric acid is at least about ¼ and less than 2, under conditions sufficient to hydrate said cellulose, and recovering the resulting hydrated cellulose.

* * * * *